United States Patent
Yaron

(10) Patent No.: US 7,615,048 B2
(45) Date of Patent: Nov. 10, 2009

(54) ENGINE WITH LIQUID PISTON

(76) Inventor: Ran Yaron, 533 22nd St., Boulder, CO (US) 80302

( * ) Notice: Subject to any disclaimer, the term of this patent is extended or adjusted under 35 U.S.C. 154(b) by 580 days.

(21) Appl. No.: 11/210,215

(22) Filed: Aug. 23, 2005

(65) Prior Publication Data

US 2005/0277914 A1    Dec. 15, 2005

Related U.S. Application Data

(62) Division of application No. 10/328,380, filed on Dec. 19, 2002, now Pat. No. 6,949,094.

(60) Provisional application No. 60/341,952, filed on Dec. 19, 2001.

(51) Int. Cl.
   *A61B 18/02*    (2006.01)
(52) U.S. Cl. .......................... 606/21; 606/20
(58) Field of Classification Search ............ 606/20–25; 347/51; 62/51.2, 293
   See application file for complete search history.

(56) References Cited

U.S. PATENT DOCUMENTS

| | | | |
|---|---|---|---|
| 4,016,722 A | 4/1977 | Niederer, Sr. |
| 4,104,507 A | 8/1978 | Tisone et al. |
| 4,296,421 A | 10/1981 | Hara et al. |
| 4,490,728 A | 12/1984 | Vaught et al. |
| 4,723,129 A | 2/1988 | Endo et al. |
| 4,742,678 A | 5/1988 | Bartholomew et al. |
| 5,104,929 A | 4/1992 | Bilkadi |
| 5,147,355 A | 9/1992 | Friedman et al. |
| 5,255,016 A | 10/1993 | Usui et al. |
| 5,275,595 A | 1/1994 | Dobak, III |
| 5,412,265 A | 5/1995 | Sickafus |
| 5,428,259 A | 6/1995 | Suzuki |
| 5,429,177 A | 7/1995 | Yaron et al. |
| 5,433,717 A | 7/1995 | Rubinsky et al. |
| 5,447,032 A | 9/1995 | Epstein et al. |
| 5,472,406 A | 12/1995 | De la Torre et al. |
| 5,522,870 A | 6/1996 | Ben-Zion |
| 5,579,654 A | 12/1996 | Longsworth et al. |
| 5,602,386 A | 2/1997 | Neuberger |
| 5,649,423 A | 7/1997 | Sniegowski |
| 5,662,590 A | 9/1997 | De la Torre et al. |
| 5,707,368 A | 1/1998 | Cozean et al. |

(Continued)

OTHER PUBLICATIONS

Allen, R. R., Meyer, J.D. and Knight, W.R., "*Thermodynamics and Hydrodynamics of Thermal Ink Jets*", Hewlett-Packard Journal, May 1985, pp. 21-27.

(Continued)

*Primary Examiner*—Michael Peffley
*Assistant Examiner*—Ronald J Hupczey, Jr.
(74) *Attorney, Agent, or Firm*—Knobbe, Martens, Olson & Bear LLP

(57) ABSTRACT

An engine comprises a liquid piston disposed within a chamber of an engine body. The chamber is defined by at least one wall. The liquid piston has one or more free surfaces that are not in contact with the chamber wall. A laser directly heats the free surface of the liquid piston. A gas spring is disposed within the chamber adjacent the free surface of the liquid piston and within the propagation path of the laser energy. The engine also includes a spring mechanism. The spring mechanism is positioned within the housing to exert pressure on another surface of the liquid piston.

3 Claims, 9 Drawing Sheets

U.S. PATENT DOCUMENTS

| | | | |
|---|---|---|---|
| 5,787,715 | A | 8/1998 | Dobak, III et al. |
| 5,891,188 | A | 4/1999 | Maytal |
| 5,901,737 | A | 5/1999 | Yaron |
| 5,935,424 | A | 8/1999 | Dyer et al. |
| 5,944,687 | A | 8/1999 | Benett et al. |
| 5,997,526 | A | 12/1999 | Giba et al. |
| 6,022,309 | A | 2/2000 | Celliers et al. |
| 6,033,371 | A | 3/2000 | Torre et al. |
| 6,106,546 | A | 8/2000 | Gregory |
| 6,139,543 | A | 10/2000 | Esch et al. |
| 6,151,901 | A | 11/2000 | Dobak et al. |
| 6,210,400 | B1 | 4/2001 | Hebert et al. |
| 6,270,476 | B1 | 8/2001 | Santoianni et al. |
| 6,283,718 | B1 | 9/2001 | Prosperetti et al. |
| 6,339,470 | B1 | 1/2002 | Papademetriou et al. |
| 6,343,852 | B1 * | 2/2002 | Yoon .......................... 347/54 |
| 6,352,535 | B1 | 3/2002 | Lewis |
| 6,383,180 | B1 | 5/2002 | Lalonde et al. |
| 6,474,783 | B1 * | 11/2002 | Pilossof et al. ................ 347/51 |

OTHER PUBLICATIONS

International Preliminary Examination Report for PCT/US02/41157, Jan. 12, 2004.

International Search Report for PCT/US02/41157, Nov. 12, 2003.

Lustgarten, Daniel L; Keane, David; and Ruskin, Jeremy; "*Cyrothermal Ablation: Mechanism of Tissue Injury and Current Experience in the Treatment of Tachyarrhythmias*", Progress in Cardiovascular Diseases, vol. 41, No. 6 (May/Jun.), 1999: pp. 481-498.

Olgin, MD., Jeffrey E., "*New Technology: Catheters, Energy Sources, Mapping*", NASAPE meeting, May 2002.

* cited by examiner

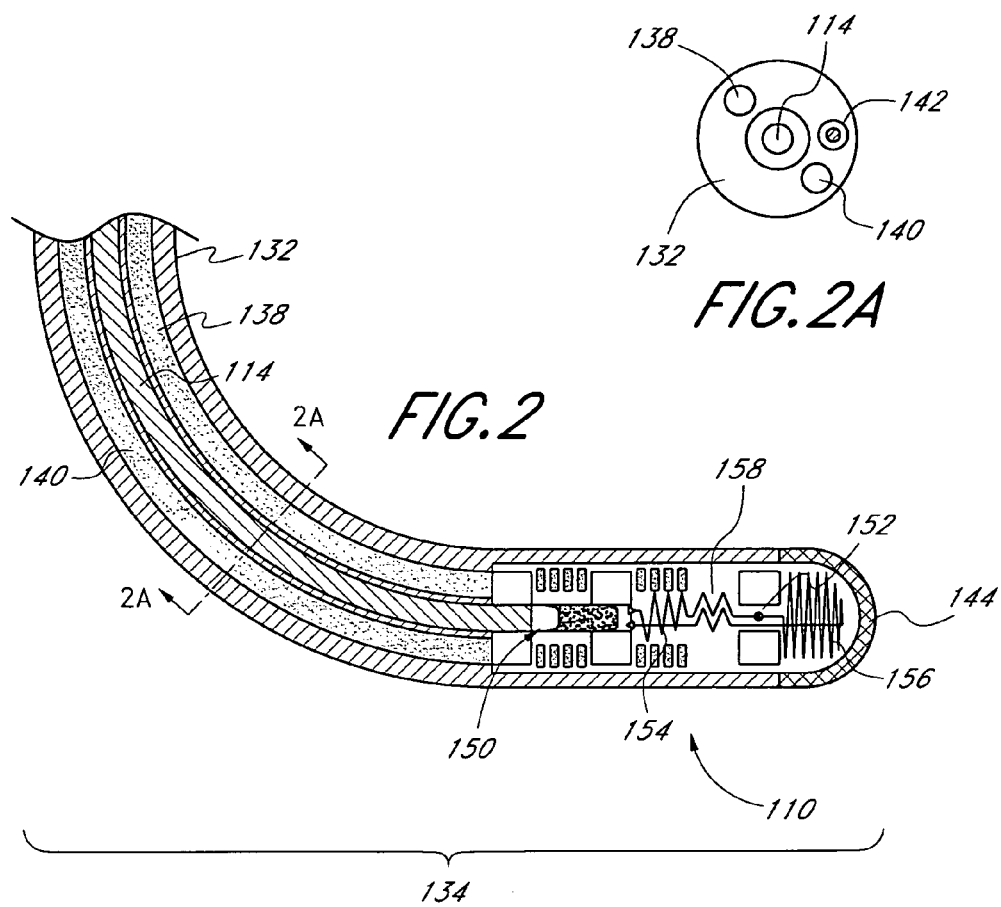
FIG.2
FIG.2A
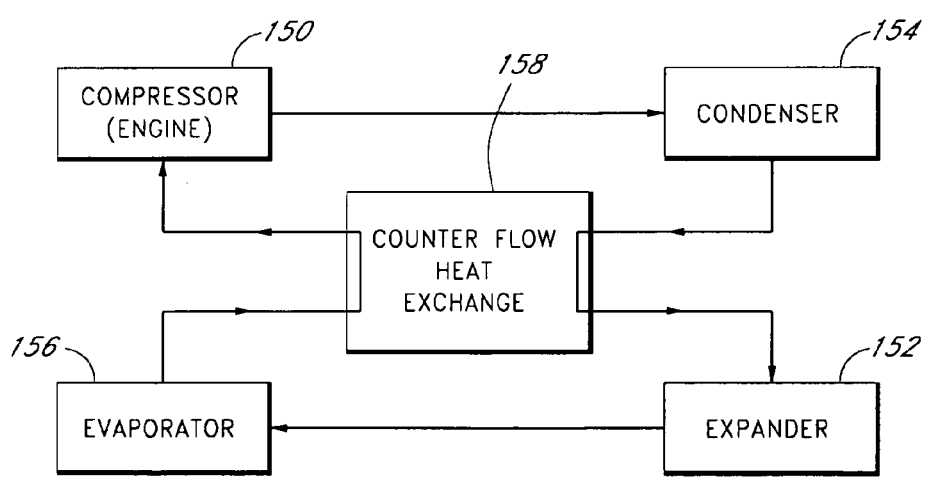
FIG.3

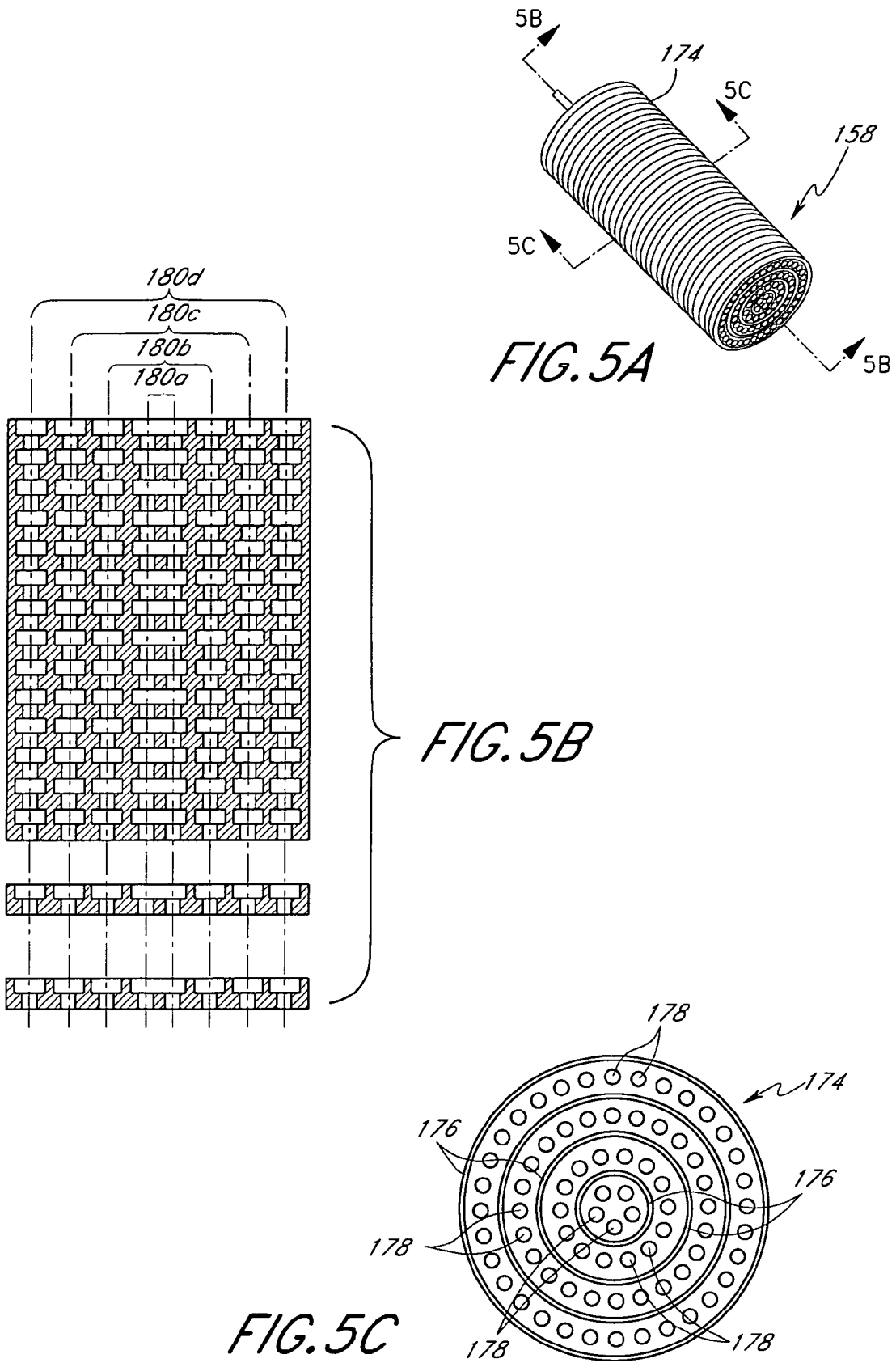

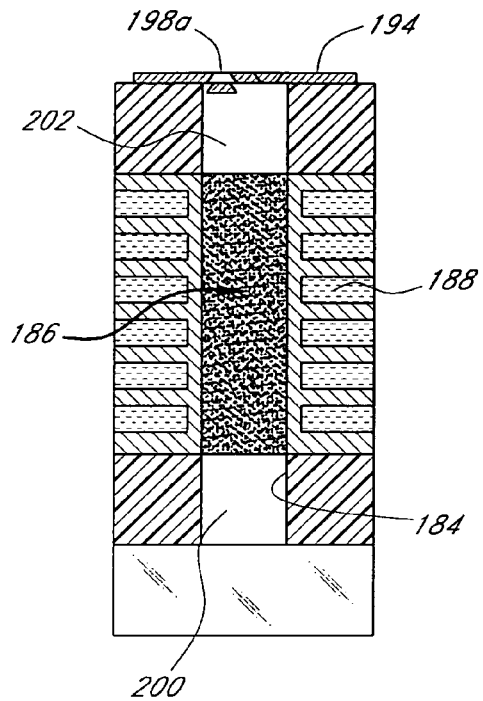
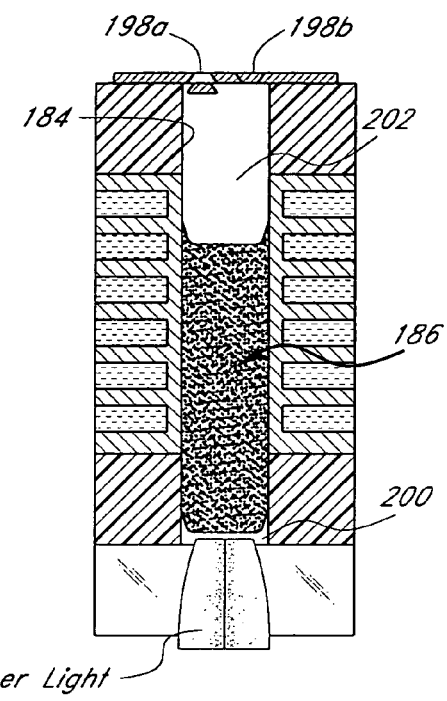
FIG.9A   FIG.9B
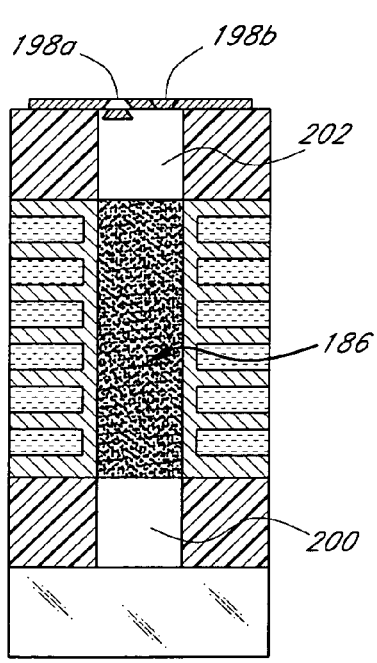
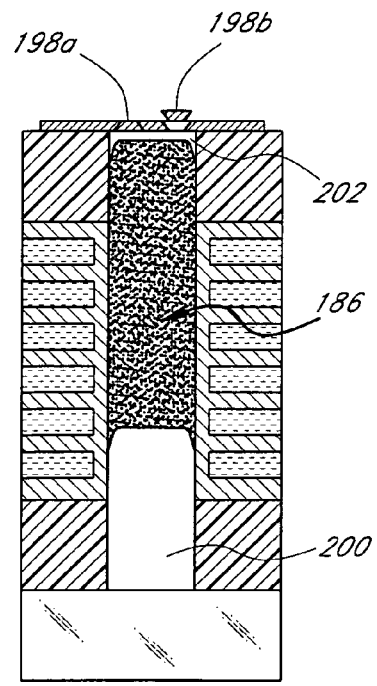
FIG.9C   FIG.9D

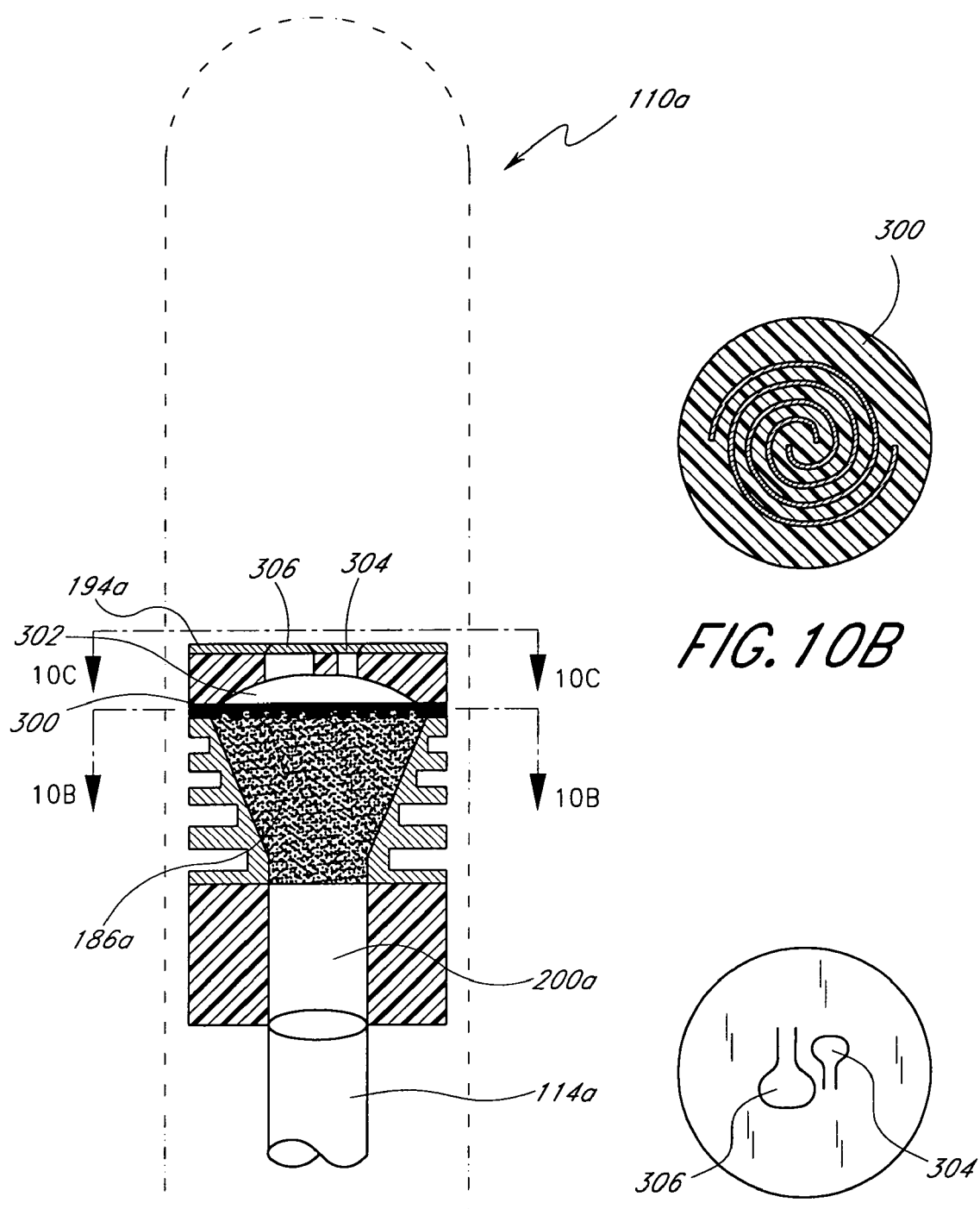

ENGINE WITH LIQUID PISTON

RELATED APPLICATION

The present application is a divisional application of U.S. patent application Ser. No. 10/328,380, filed Dec. 19, 2002, now U.S. Pat. No. 6,949,094 entitled MINIATAURE REFRIGERATION SYSTEM FOR CRYOTHERMAL ABLATION CATHETER, which is based upon and claims priority under 35 U.S.C. § 119(e) to U.S. Provisional Application No. 60/341,952, filed Dec. 19, 2001, entitled LASER REFRIGERATOR, which are hereby incorporated by reference.

BACKGROUND OF THE INVENTION

1. Field of the Invention

The present application relates to cryothermal ablation catheters, as well as to miniature refrigerators and miniature engines for producing mechanical force or effecting mechanical work.

2. Description of the Related Art

Ablation catheters are commonly used to treat arrhythmias by destroying or disrupting cardiac tissue associated with the source of the arrhythmias or their conductive pathways. At present, most ablation procedures are performed using an ablation catheter in which radio frequency (RF) current is passed through tissue contacting the catheter tip to create lesions by means of hyperthermia. Use of such RF current involves risk of char and coagulum formation, particularly if the lesions created are more extensive than focal lesions, such as may be required for circumferential lesions in the pulmonary veins. Formation of char and coagulum is ordinarily caused by poor tissue contact with the catheter tip and creates an undesirable risk of thromboembolic stroke. Other risks of RF ablation include possible unroofing of the endothelium or producing pulmonary vein contraction.

Cryothermal ablation solves many of the problems associated with RF ablation. Destruction of tissue by freezing leaves the connective tissue matrix intact. Lesions are created by rupturing cell membranes, and damaged cells are replaced by fibrotic tissue. There is no formation of char or coagulum, and thus the risk of thromboembolic stroke is low. Additionally, as the tissue is cooled, the catheter tip adheres to the tissue which provides improved stability.

Although cryothermal ablation provides many advantages over RF ablation, it has proven difficult to implement. Cryocatheters today typically comprise a cooling system that provides cooling power by pumping a vaporized refrigerant through a lumen in the catheter to a Joule-Thomson expander located at the catheter distal end. The length of the catheter (often 1 meter or longer) and the small diameter of the lumen within the catheter (often less than 1 mm in diameter) limit the flow rate through the Joule-Thomson expander. Additionally, the pressure of the vapor returning through the catheter must be held under 1 atmosphere to meet FDA requirements, which further limits the flow rate through the Joule-Thomson expander. The cooling power of the system consequently is limited to about 2 Watts, which limits the depth of tissue ablation to about 4 mm.

Accordingly, there is a need in the art for a cryocatheter that does not require transport of refrigerant along the length of the catheter so as to permit increased refrigerant flow rates. At a more fundamental level, there is a need for a miniature engine that can be adapted to, among other things, drive a miniature refrigeration system in the tip of a cryocatheter.

SUMMARY OF THE INVENTION

The preferred embodiment of the present invention overcomes disadvantages of conventional cryocatheters by housing a miniature refrigerator in the tip of a cryocatheter and powering the refrigerator using electromagnetic radiation delivered through a waveguide. A summary of a preferred embodiment is provided followed by a summary of inventive aspects.

The preferred miniature refrigerator avoids the need to transport refrigerant through the length of the cryocatheter by housing the refrigerant circulation system entirely in the tip of the catheter. It utilizes a unique engine that is a revolutionary breakthrough in miniaturization. The preferred engine harnesses the power of a laser by converting electromagnetic energy into mechanical work. It provides an enormous gain in delivered power per unit volume compared to other power sources such as electric motors. Conversion of optical energy to mechanical energy is accomplished by directing laser energy through a gas spring onto a free surface of a liquid mass to non-uniformity heat the liquid mass. The heating is very rapid (e.g. <100 nsec) such that the portion of liquid exposed to radiation quickly reaches its superheat limit and explosively boils. The explosion propels the remaining portion of the liquid (which functions as a piston) to adiabatically compress refrigerant in a compression chamber. The compression results in a pressure increase, thus providing a restoring force which pushes the liquid towards its original position and against the gas spring, which allows the original position to be overshot. At the point of maximum displacement, the laser is fired again and the cycle repeats. The inertia of the liquid and the compression of the vapor cause the device to function as an oscillator which possess a natural frequency. The energy lost during each oscillation is replenished by tuning the repetition rate of the laser pulses to the natural frequency. By firing the laser at (or just after) the point of maximum displacement, resonant operation is established, and the oscillations will persist.

Inventive aspects associated with the embodiments described herein are abundant. In one such inventive aspect, a cryo-medical apparatus comprises an elongated body defined between a proximal end and a distal end. A closed-cycle miniature refrigeration unit, which includes a compressor and at least a first heat exchanger, is disposed at the distal end. A waveguide for conducting electromagnetic energy extends from the proximal end of the elongated body to the distal end. The waveguide provides electromagnetic radiation to drive the compressor.

In another aspect of the invention, a cryo-medical system comprises a cryo-apparatus which includes an elongated body defined between a proximal end and a distal end. A closed-cycle miniature refrigeration unit, which includes a compressor in at least a first heat exchanger, is disposed at the distal end. A waveguide extending from the proximal end of the catheter body to the distal end conducts electromagnetic energy to drive the compressor. A coupler coupled the source of electromagnetic radiation to the waveguide.

A further aspect of the invention is a closed-cycle miniature refrigeration system comprising a compressor having a housing defining at least one chamber. A liquid piston is positioned to reciprocate within the chamber. A source of electromagnetic radiation energizes the liquid piston by exposing a portion of the liquid piston to electromagnetic radiation. The source of electromagnetic radiation drives the liquid piston to reciprocate within the chamber such that the liquid piston compresses a working fluid. A heat exchanger is in communication with the compressor.

Yet another aspect of the invention is a medical apparatus having an elongated body defined between a proximal end and a distal end. An engine is disposed within the elongated body and preferably at the distal end of the elongated body. The engine includes a housing defining a chamber and a liquid mass position within the chamber. A waveguide extends from the proximal end of the elongated body to the distal end and conducts electromagnetic radiation such that the liquid mass is heated non-uniformly.

An additional aspect of the invention is an engine comprising a housing defining a chamber. A liquid mass is positioned to oscillate within the chamber at a frequency. A source of electromagnetic radiation energizes the liquid mass by exposing a portion of a liquid mass to the radiation. The radiation causes the liquid mass to be driven at the frequency of oscillation. Preferably, the frequency of oscillation is a natural frequency of the liquid mass in the housing.

In yet another aspect of the invention, an engine comprises a housing defining a chamber. A liquid mass is disposed within the chamber. The source of electromagnetic radiation energizes the liquid mass by exposing a portion of the liquid mass to the electromagnetic radiation. A gas spring is disposed within the chamber and within a propagation path of the electromagnetic radiation.

A further aspect of the invention is an engine which comprises a housing defining a chamber which includes first and second end sections and an intermediate section. A liquid mass is disposed within the chamber. Each of the first and second end sections of the chamber is formed of a material having a low affinity for the liquid of the liquid mass, and the intermediate section is formed of the material having a higher affinity for the liquid of the liquid mass. A source of electromagnetic radiation heats a portion of the liquid mass.

In an additional aspect of the invention, a method of oscillating a liquid mass within a housing comprises converting a portion of the liquid mass to a gas phase to propel the remainder of the liquid mass within the housing. A substantial portion of the gas phase portion is reconverted back to the liquid phase, and the converting and reconverting are repeated to cause the liquid mass to oscillate.

A further aspect of the invention is a method comprising oscillating a liquid mass within a housing by converting electromagnetic energy into mechanical work and heat. The oscillations are stabilized by removing heat such that the oscillations reach steady state.

Another aspect of the present invention involves an engine comprising a housing having chamber wall that defines a chamber within the housing. A liquid piston is disposed within the chamber and has at least one free surface not in contact with the chamber wall. A source of laser energy is positioned to directly heat the free surface of the liquid piston. The engine also includes a gas spring and a spring mechanism. The gas spring is disposed within the chamber adjacent the free surface of the liquid piston and within the propagation path of the laser energy. The spring mechanism is also positioned within the housing and is arranged to exert pressure on another surface of the liquid piston. Preferably, the gas spring and spring mechanism are symmetrically disposed relative to the liquid piston.

BRIEF DESCRIPTION OF THE DRAWINGS

These and other features, aspects and advantages of the present invention will be further understood with reference to preferred embodiments, which are illustrated in the accompanying drawings. The illustrated embodiments are merely exemplary and are not intended to limit of the scope of the present invention. The drawings of the illustrated embodiments comprise 24 figures.

FIG. 2 is an enlarged sectional schematic view of a distal end of the cryocatheter.

FIG. 2A is a cross-section of the cryocatheter taken along line 2A-2A of FIG. 2.

FIG. 3 is a block diagram illustrating the components of a closed loop refrigeration system disposed at the distal end of the cryocatheter.

FIG. 5A is an enlarged perspective view of another heat exchanger of the refrigeration system that can be used in the place of the heat exchanger illustrated in FIG. 4A. In particular, FIG. 5A illustrates a stacked etched-disk heat exchanger configured in accordance with another preferred mode of the refrigeration system.

FIG. 5B is a partially exploded, cross-sectional view of the heat exchanger of FIG. 5A taken along line 5B-5B. For illustration purposes only, FIG. 5B shows two disks of the stacked as spaced apart from the body of the stack to illustrate the cross-section of an individual disk and to illustrate the structural identicalness between the disks in the stack.

FIG. 5C is a cross-sectional view of the heat exchanger of FIG. 5A taken along line 5C-5C and illustrates an annular face of a disk in the stack.

FIGS. 9A through 9D are schematic sectional views of the compressor engine of FIG. 8 shown at four different stages of an operation cycle.

FIG. 10A is a schematic illustration of a compressor engine configured in accordance with another embodiment of the present invention.

FIG. 10B is a cross section of the compressor engine of FIG. 10A taken along line 10B-10B.

FIG. 10C is a plan view of a distal plate of the compression engine of FIG. 10A as viewed in the direction of section 10C-10C, and illustrates a valve mechanism that regulates fluid flow into and out of the compressor engine.

DETAILED DESCRIPTION OF THE PREFERRED EMBODIMENTS

A miniature engine is particularly well suited to function as a compressor in conjunction with a miniature refrigeration system and, in particular, in conjunction with a miniature refrigeration system employed with a cryoablation catheter. The illustrated preferred embodiments are thus of a cryoablation system. The miniature engine, however, can be used in a variety of other applications including, for example, but without limitation, micro-actuators (e.g. linear actuators), micro-pumps (e.g., for drug delivery), micro-acoustical generator (e.g., an ultrasound transducer), micro-injectors (e.g., for inkjet and fuel injection applications), and optical switches. Additionally, the described miniature refrigeration system can be used in other applications as well, such as, for example, but without limitation, in the cooling of high power density electronics, solid-state lasers, IR sensors and similar devices. The following description of the preferred embodiments thus represents only one possible application of the engine described herein in a biomedical application relating to cryoablation of cardiac tissues for the treatment of arrhythmias.

Cryoablation System

Figure 1:
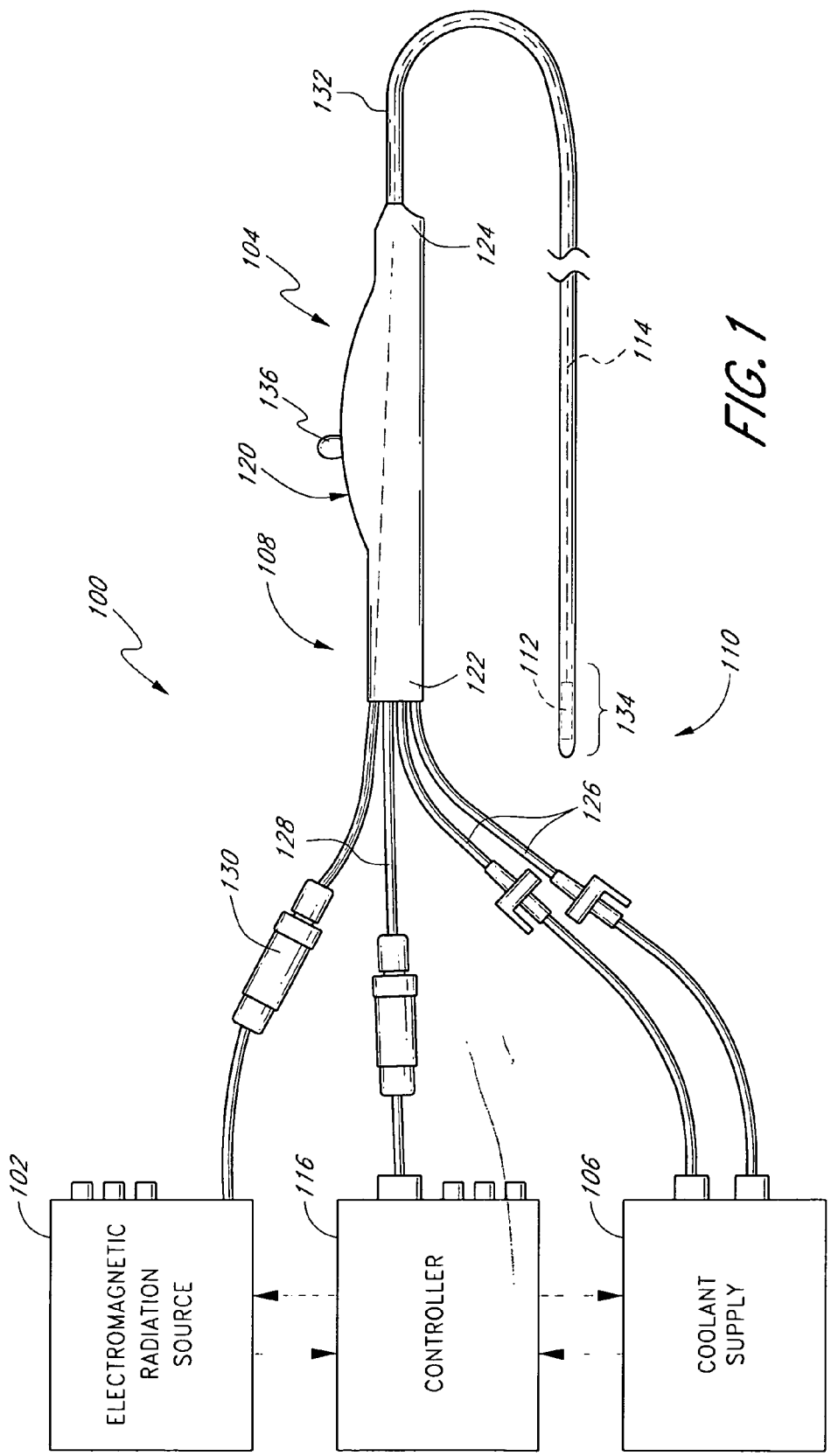
FIG. 1 is schematic illustration of a cryothermal ablation system including a cryocatheter, which is configured in accordance with a preferred embodiment of the present invention.

As seen in FIG. 1, the cryothermal ablation system 100 includes a source of electromagnetic radiation 102, a cryocatheter 104, and a source of fluid coolant 106. The cryocatheter 104 has a proximal end 108 and a distal end 110 and includes a miniature, closed-loop refrigeration system 112 disposed within the catheter 104. In the illustrated embodiment, the refrigeration system is disposed at a distal end 110 of the catheter 104. A waveguide 114 within the catheter 104 couples the source of electromagnetic radiation 102 to the refrigeration system 112 so as to power the refrigeration system 112. The coolant source 106 provides coolant to the refrigeration system 112 to remove heat build-up from components of the system 112 and from the refrigerant circulating just at the distal end of the catheter 104.

In the illustrated embodiment, a laser provides laser light to power the refrigeration system 112. Other sources of electromagnetic radiation, however, can be used in other embodiments and applications. For example, electric discharge, microwave or X-ray radiation can be used to power the refrigeration system.

The source of coolant 106 preferably provides a cooled or chilled liquid coolant (e.g., saline), which flows through at least the distal end 110 of the catheter 104 when the catheter 104 is connected to the coolant source 106. The coolant source 106 can either forms a closed-loop cooling system with the cryocatheter 104 or an open-loop cooling system with the cryocatheter 104. In the illustrated embodiment, a closed-loop system is formed with the coolant circulating between the catheter 104 and the coolant source 106. For this purpose, the coolant source 106 preferably comprises a heat exchanger in order to control the temperature of the coolant entering the catheter 104. The coolant, however, need not be chilled to temperatures required for cryoablation. The coolant rather functions to remove heat from components of the miniature refrigeration system 112, as will be described in greater detail.

The ablation system 100 can also include a controller 116 that controls the operation of the laser 102 and the coolant supply 106 in response to manual control, as well as possibly in response to one or more feedback signals from various sensors and monitors used in combination with or integrated into the cryoablation system 100. For example, various thermocouples and mapping electrodes can be incorporated onto the distal end 110 of the cryocatheter 106, as known in the art, in order to provide temperature information, to assess ablation efficacy, and to locate foci of arrhythmia prior to ablation.

Cryocatheter

As seen in FIG. 1, the cryocatheter 104 includes a handle 120 having a proximal end 122 and a distal end 124, and is configured to be comfortably held by a practitioner during a treatment procedure involving cryoablation. A plurality of conduits, conductors, and wires extend from the proximal end of the handle 120 for connection to the laser 102, the coolant supply 106 and the controller 116. In the illustrated embodiment, a plurality of conduits 126 connect the coolant supply 106 to the catheter handle 120, a wiring harness 128 connects the handle 120 to the controller 116, and an optical coupler 130 couples the waveguide 114 to the laser 102. These conduits, conductors, waveguide and wires extend through the handle 120 to the handle's distal end 124.

An elongated, flexible catheter body or shaft 132 extends from the distal end 124 of the handle 120. The catheter 104 preferably has a sufficient length to be introduced into the heart (e.g., into the left atrium or right ventricle) through a percutaneous translumenal procedure. Moreover, for certain applications, the cryocatheter 104 can be designed to access the left atrium in a transeptal procedure. Accordingly, the distal portion of the catheter body 132 is preferably flexible; however, the proximal portion of the catheter body 132 can be more rigid, as known in the art.

In the illustrated embodiment, the catheter 104 includes a deflectable distal segment 134 in order to steer the catheter and to position the cryoablation element(s) of the catheter 104. For this purpose, the catheter 104 includes one or more pull wires that extends through the catheter body 132 from the handle 120 and that are affixed to one or more locations at the distal segment 134. The pull wire or wires are connected at their proximal ends to a manual controller 136, such as a thumb lever. The thumb lever 136 when moved tightens the pull wires to deflect the distal segment 134 of the catheter body 132, as well known in the art. In this manner, the practitioner can steer the catheter 104 through the vascular structure and introduce the catheter into one of the heart chambers (e.g., into the left atrium with the aid of a transeptal sheath).

Other positioning mechanism, however, can be used with the catheter 104, either as an alternative to or in addition to the pull wire steering mechanism. For example, the catheter can be slidably coupled with a guidewire and, for this purpose, can include a guidewire lumen that extends at least a substantial length of the catheter. The catheter can be slidably coupled to the guidewire externally of the patient's body in a "back-loading" technique after the distal end of the guidewire is first positioned at the target site. Other guidewire tracking designs may also be suitable substitutes, such as, for example, catheter devices known as "rapid exchange" or "monorail"

variations wherein the guidewire is only housed within a lumen of the catheter in a distal region of the catheter. Additionally, the catheter (or guidewire) can be guided to and positioned at the target site by the use of sub-selective sheaths for advancing the guidewire and/or catheter into the desired location and position within the heart.

The waveguide 114 extends through the catheter body 132 from its proximal end to the distal segment 134 of the catheter and cooperates with the refrigeration system 112. The waveguide 114 in the illustrated embodiment comprises an optical fiber that has a core and a cladding; however, other types of waveguides (both solid and hollow) can be used in other applications. Advantageously, the optical fiber 114 carries optical energy the length of the catheter 104 with minimal attenuation.

The catheter body 132 houses the waveguide 114 and includes a plurality of lumens. Each lumen extends from a proximal port at the proximal end of the catheter body to a distal port located at or near the distal end of the catheter. Some or all of the lumens can be arranged in a side-by-side relationship, in a coaxial relationship or in any of a wide variety of configurations that will be readily apparent to one of ordinary skill in the art.

With reference to FIGS. 2 and 2A, a first lumen 138 in the illustrated embodiment delivers coolant to the distal end 110 and a second lumen 140 returns the coolant to the coolant source 106. Neither of these lumens 138 140 need to be significantly insulated because the coolant supplied and returned through these lumens has a temperature well above that capable of damaging tissue or blood cells. A third lumen 142 houses the pull wire.

Additional lumens can be provided for additional purposes. For example, an additional lumen can be arranged adjacent to or coaxially about the waveguide 114 and connected to a supply of cooling fluid, such as gas, in order to cool the waveguide. In addition to or in the alternative to such cooling fluid, the first and second lumens 138, 140, which carry the liquid coolant, can be used to cool the waveguide. Further lumens can carry electrical wires or other conductors that are connected to sensors (e.g., thermocouples, thermisters, mapping electrodes, ultrasound imaging transducers, etc.) disposed at the distal end 110 of the catheter 104. A lumen(s) can also be provided to provide an inflation medium in variations of the cryocatheter that include one or more inflatable balloons. Aspiration, irrigation, and perfusion lumens can similarly be incorporated into the catheter body. Accordingly, in addition to the illustrated lumens, one or more additional lumens or conduits can be provided for additional connections to the distal end 110 of the catheter 104.

The catheter body 132 accordingly includes a number of internal components housed within the internal structure of the body and can also include various layers over the internal structure. Any of a variety of different polymeric materials, which are known by those of skill in the art to be suitable for catheter body manufacture, can be used to form the catheter body 132. For example, the body 132 may be formed out of polymers such as polyethylene, PEBAX (Atochem, France), polyimide, polyether etherketone, and the like. Additionally, the catheter body 132 can also includes a biocompatible, leak-proof outer jacket formed of any of a variety of materials, such as, for example, but without limitation, nylon, PEBAX, Teflon, or other suitable plastic or polymer materials, as well known to those skilled in the art. The catheter preferably is made in accordance with known manufacturing techniques.

The catheter body 132 also preferably has sufficient structural integrity, or "stiffness," to permit the catheter 104 to be pushed through the vasculature to target site without buckling or undesirable bending of the body 132. It is also desirable, however, for the body 132 to be fairly flexible near its distal end 110, so that the distal segment 134 of the catheter 104 can be navigated through tortuous blood vessel networks. Thus, in one preferred embodiment, the body 132 of the catheter 104 is formed from a polymer such as polyethylene or PEBAX made to have variable stiffness along its length, with the proximal portion of the body being less flexible than the distal portion of the body. Advantageously, a body of this construction enables a user to more easily insert the tubular body into vascular networks. Additionally, the catheter body, or at least certain sections thereof, can be include reinforcing braid or coil incorporated into its wall structure. The reinforcing can be formed of metal or of various polymers.

As seen in FIG. 2, the distal end 110 of the illustrated catheter 104 has a heat transfer element 144 with a blunt contact tip. The distal end 110, however, can have other configurations. For example, the distal end 110 can have a shaped tip design, such as, for example a loop design that can be expanded or manipulated as known by those of ordinary skill in the art. A shaped stylet can also be used with the catheter to vary the shape of the distal end 110 of the catheter in order to hold a particular shape during an ablation procedure to ablate a desired pattern (e.g., arcuate or circular), or for steering or positioning purposes. Additionally, the distal end 110 can include a plurality of heat transfer elements that the refrigeration system 112 cools.

Refrigeration System

With reference to FIGS. 2 and 3, the closed-cycle refrigeration system 112 includes at least a compressor engine 150 and a heat exchanger to cool the heat transfer element(s) 144 at the distal end 110 of the catheter 104. In the illustrated embodiment, the refrigeration system also comprises a second heat exchanger, an expander 152, and preferably a third heat exchanger. One of the heat exchangers functions as a condenser 154, another heat exchanger functions as an evaporator or boiler 156, and the third heat exchanger functions as a counter-flow heat exchanger 158. A refrigerant circulates through the closed-cycle system.

The compressor engine 150 draws in saturated refrigerant into the compressor 150 from an inlet side of the compressor engine 150. The compressor engine 150 compresses the vapor isentropically to a superheated vapor, which then flows to the condenser 154 on an outlet side of the compressor engine 150. The refrigerant vapor then enters a condenser 154, where heat is removed at constant pressure until the fluid becomes a saturated liquid. The liquid then passes through the high temperature side of the counter-flow heat exchanger 158 and into the expander 152. The liquid expands adiabatically in order to bring the fluid to a lower pressure. The liquid refrigerant thence passes through the evaporator 156 at a constant pressure. Heat flows into the evaporator 156 from the heat transfer element(s) 144 (FIG. 2) and vaporizes the fluid to the saturated-vapor state for reentry into the compressor 150. In particular, the liquid absorbs heat from an inner surface of the heat transfer element 144, thereby cooling the outer surface and vaporizing the liquid refrigerant within the evaporator 156. The fluid enters the low temperature side of the counter-flow heat exchanger 158 before it enters the compressor 150. The counter-flow heat exchanger 158 is used to cool further the liquid refrigerant before it enters the expander 152 and to heat the vapor before it returns to the compressor 150.

The condenser 154 receives coolant from the catheter coolant delivery lumen 138 and discharges it to the compressor 150 for cooling purposes or returns it to the coolant return lumen 140. Alternatively, the condenser 154 can receive coolant from the compressor 150.

The expander 152 can include one or more valves, orifices, capillary tubes or similar types of flow restrictions. In one preferred mode, the expander 152 is a Joule-Thomson expansion device.

Figure 4A:
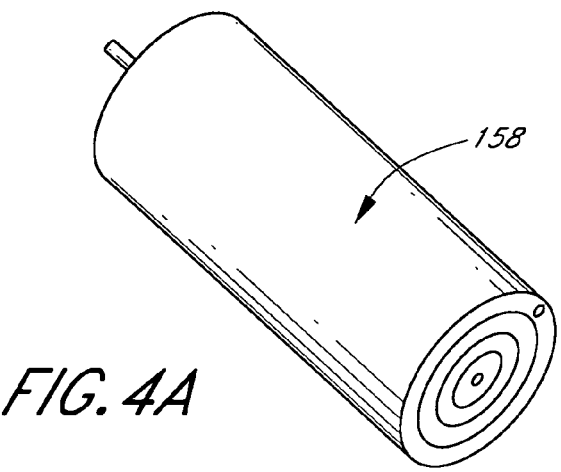
FIG. 4A is an enlarged perspective view of a heat exchanger of the refrigeration system that is configured in accordance with a preferred mode of the refrigeration system.
Figure 4B:
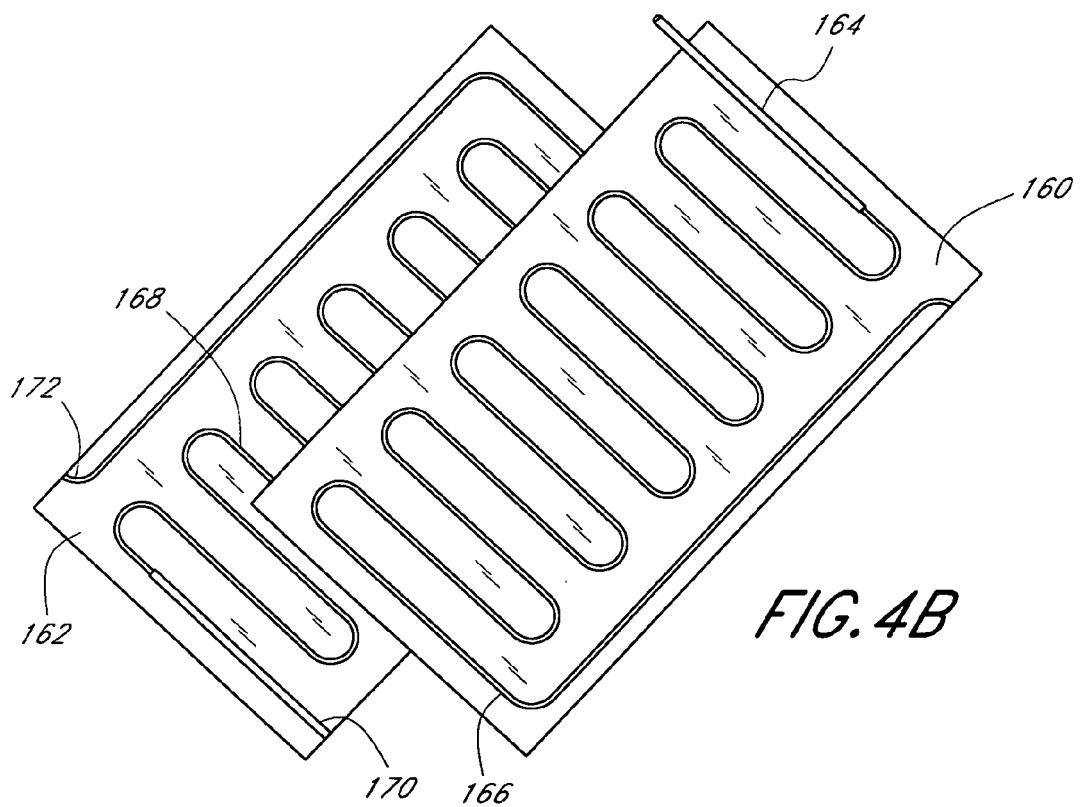
FIG. 4B is an exploded perspective view of etched foils of the heat exchanger of FIG. 4A in an unformed, pre-assembled state.

Each of the heat exchangers—the condenser 154, the evaporator 156, the counter-flow heat exchanger 158—can be manufactured as miniature structures with high surface area using photoetching technology as taught by U.S. Pat. No. 5,935,424, the disclosure of which is hereby incorporated by reference. An example of a suitable heat exchanger structure for the counter-flow heat exchanger 158 is illustrated in FIGS. 4A and 4B while, in FIGS. 5A through 5C, an example of the condenser 154 is illustrated. The size, shape and relative scale of the illustrated heat exchangers are only by way of examples, and the heat exchangers can be configured and constructed to meet specific design requirements, e.g., to fit within a distal end of a catheter having an overall outer diameter of 3 mm. Additionally, either of the illustrated heat exchanger structures can be used to form the condenser 154, the evaporator 156 or the counter-flow heat exchanger 158. The illustrated heat exchanger structures also allow for the integration of two or more of the refrigerator's heat exchangers 154, 156, 158 into a single structural unit (e.g., the stacked disk structure described below can be configured so as to form both the condenser and the counter-flow heat exchanger).

With reference to FIGS. 4A and 4B, the counter-flow heat exchanger 158 is formed by at least two foil sheets 160, 162. A discharge from the condenser 154 is schematically illustrated as connecting to an inlet 164 of a microchannel 166 that is etched onto the first sheet 160. The second sheet 162 has a similar microchannel 168 etched onto it, with an inlet 170 and an outlet 172. The inlet 170 communicates with the evaporator 156 and the outlet 172 communicates with the inlet side of the compressor engine 150. The microchannels 166, 168 preferably are etched only halfway through the respective foil sheets 160, 162. The foil sheets 160, 162 can be joined (e.g., diffusion bonded) together in the orientation shown. The assembly then can be rolled, as shown in FIG. 4A, to construct a cylindrical heat exchanger.

FIGS. 5A through 5C illustrate a variation of the counter-flow heat exchanger 158. In this embodiment, the heat exchanger 158 comprises a plurality of stacked disks 174. Preferably, at least most of the disks 174 have the same configuration, and end caps (not shown) close the end disks in the stack. Each disk 174 includes a plurality of annular ribs 176 that are concentrically arranged, as best seen in FIG. 5C. A plurality of openings 178 are disposed between each pair of adjacent ribs 176. When the disks 174 are stacked and joined together, as seen in FIG. 5B, the stacked assembly forms four annular flow channels 180a, 180b, 180c, 180d. In each flow channel 180a-d, the fluid flows through the disk openings 178 and then into an annular space defined between adjacent disk ribs 176 (which ribs 176 may be of the same disk 174 or of the adjacent disk 174 depending upon the flow direction). The ribs 176 and the openings 178 preferably are formed on and through the disk 174, respectively, by photo-etching, laser-drilling, EDM (electrical discharge machining) and/or similar processes.

When this heat exchanger structure is used as the condenser 154, the inner channel 180a preferably carries incoming coolant from the coolant lumen 138, and the adjacent channel 180b delivers high pressure refrigerant from the compressor 150. The next channel 180c carries the returning coolant, which is delivered either to the compressor 150 for cooling purposes or to the coolant return lumen 140. The outermost channel 180d returns low pressure vapor to the compressor 150. Of course, where this heat exchanger structure is used for other purposes, for example, as the counter-flow heat exchanger, the disk stack can define fewer channels (e.g., two channels).

While the structure of the evaporator 156 can take the form of either of the heat exchanger embodiments just described, its structure preferably corresponds to the configuration of the heat transfer element(s) 144 that contacts the targeted tissue during a cryoablation procedure. The evaporator 156 thus is preferably configured to maximize contact between the microchannels that form the evaporator 156 (and through which refrigerant passes) and the inner surface or surfaces of the heat transfer element(s) 144.

Figure 6A:
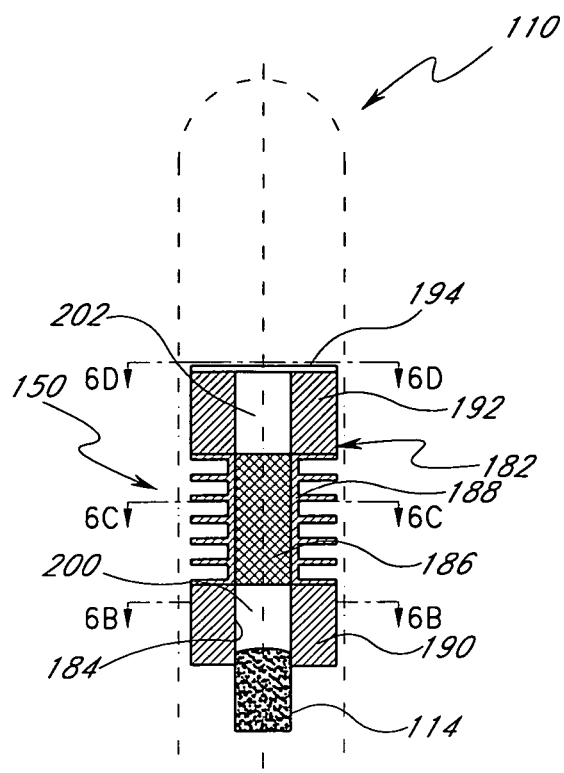
FIG. 6A is a schematic view of the distal end of the cryocatheter and schematically illustrates a compressor engine of the refrigeration system.
Figure 6B:
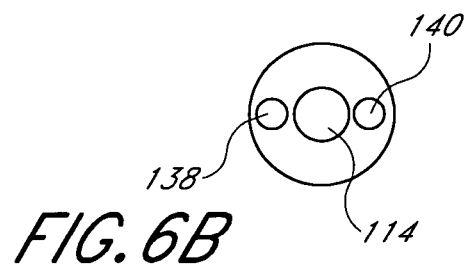
FIG. 6B is a schematic cross-sectional view of the distal end of the cryocatheter taken along line 6B-6B of FIG. 6A and schematically illustrates the construction of the catheter proximal of the compressor engine. Only those lumens associated with the compressor engine have been illustrated.
Figure 6C:
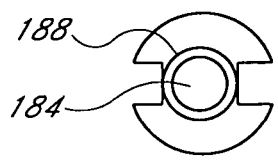
FIG. 6C is a schematic cross-sectional view of the distal end of the cryocatheter taken along line 6C-6C of FIG. 6A and illustrates the construction a central part of a housing of the compressor engine.

With reference to FIG. 6A, the compressor engine 150 of the system 112 includes a housing 182 that defines a chamber 184 and a liquid piston 186 that reciprocates within the chamber 184. In the illustrated embodiment, the chamber 184 has a cylindrical shape; however, other shapes are practicable. While the engine 150 can be employed on larger scales, the inside diameter of the cylindrical chamber 184 for its application in a catheter is preferably between about 50 μm and 5 mm, more preferably less than about 2 mm, and most preferably generally not greater than 1 mm. The small diameter cylinder 184 also provides a capillary action to help maintain the integrity of the liquid piston 186 during operation.

The cylinder chamber 184 has sufficient length to accommodate the piston 186 and to provide for its reciprocation in the chamber 184. The cylinder chamber length preferably provides the piston 186 with a sufficient stroke for the compressor engine 150 to compress and pump an amount of refrigerant necessary to cool the heat transfer element(s) 144 to a desired temperature (e.g., to −100° C.) and to actuate the valves of the compressor. For the present application in a cryocatheter, the length of the engine chamber 184 is preferably less than 10 mm, and more preferably less than about 5 mm.

The housing 182 preferably is constructed to cause the liquid piston 186 to migrate toward a generally central position within the chamber 184 when the engine is not operating. Accordingly, different parts of the housing walls preferably exhibit different affinities for the liquid of the liquid piston 186. In the illustrated embodiment, the housing comprises at least three parts that define the cylinder chamber 184: a central part 188 formed by a tube having high affinity for the liquid of the liquid piston 186; a proximal part 190 formed by a tube having low affinity for the liquid; and a distal part 192 formed by a tube also having a low affinity for the liquid. Either the material of the tubes or coatings on the tubes can have the desired affinities for the liquid.

The proximal part 190 and the distal part 192 are preferably made of thermally insulating material with an inner surface having a low affinity for the liquid, resulting in close to adiabatic compression and expansion of the vapor in those chambers. One suitable material is polytetrafluoroethylene (PTFE), available commercially as Teflon™ from E.I. du Pont and Nemours and Company. The central part 188, in addition to having a high affinity for the liquid, preferably is made of a thermally conductive material, such as, for example, copper.

The ends of the cylinder 184 also preferably have low affinities for the liquid of the liquid piston 186. The proximal end of the cylinder 184 preferably is closed by the distal end of the optical fiber 114 or by a lens (e.g., a collimating lens) or an intermediate transmitter that directs the laser light into the chamber 184 through the proximal end. In the illustrated embodiment, the distal end of the optical fiber 114 seals against the housing 182 at the proximal end thereof. The housing can additionally comprise a window element. In this variation of the housing construction, the window element would be in communication with the optical fiber and would seal the proximal end of the chamber.

Figure 6D:
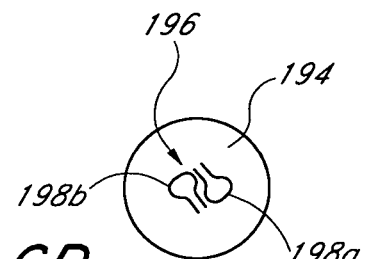
FIG. 6D is a schematic cross-sectional view of the distal end of the cryocatheter taken along line 6D-6D of FIG. 6A and illustrates the construction of a valve mechanism of the compressor that is configured in accordance with a preferred mode of the refrigeration system.

In the illustrated embodiment, a distal disk or plate 194 closes the distal end of the chamber 184. The distal plate 194 includes a valve mechanism 196 that selectively permits the refrigerant to flow into and out of the chamber 184. FIGS. 6A and 6D illustrates a compressor engine 150 in which one-way check valves 198a, 198b serve as the inlet and outlet to the chamber 184. A suction valve 198a permits refrigerant to flow from the evaporator 156 into the distal space of the chamber 184, and a discharge valve 198b permits refrigerant to flow from the distal space toward the condenser 154. Neither valve 198a, 198b, however, permits flow in an opposite direction. The valve plate 194 preferably is formed of a superelastic, shape memory material, such as Ni—Ti alloy, available commercially as Nitinol™. The valves 198a, 198b are etched in the desired configurations. The surface of the distal plate 194 that faces into the chamber preferably is coated with a material that has a low affinity for the liquid of the liquid piston 186.

Figure 7A:
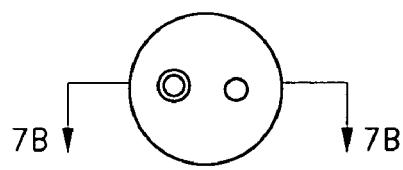
FIG. 7A is a sectional view that is similar to that of FIG. 6D and illustrates the construction of another valve mechanism that can be used with the compressor.
Figure 7B:
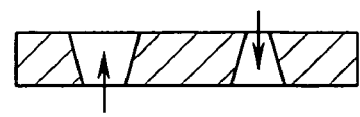
FIG. 7B is a cross-sectional view of the valve mechanism taken along line 7B-7B of FIG. 7A.
Figure 7C:
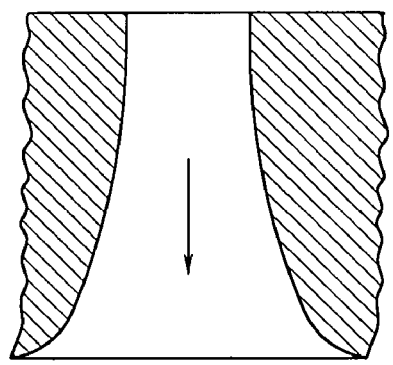
FIG. 7C is an enlarged cross-sectional view of a jet valve to illustrates a variation of a valve design for the valve mechanism illustrated in FIGS. 7A and 7B.
Figure 7D:
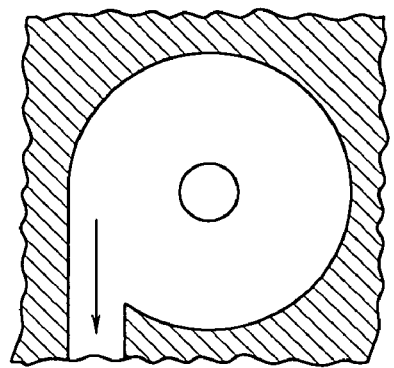
FIG. 7D is an enlarged cross-sectional view of a vortex valve to illustrate another variation of a valve design for the valve mechanism illustrated in FIGS. 7A and 7B.

FIGS. 7A and 7B illustrate another form of a one-way or check valve that employ no moving parts. Through well known principles of fluid dynamics, either a jet valve (FIG. 7C) or a vortex valve (FIG. 7D) can also provide only one-way flow from and to the compressor.

Figure 8:
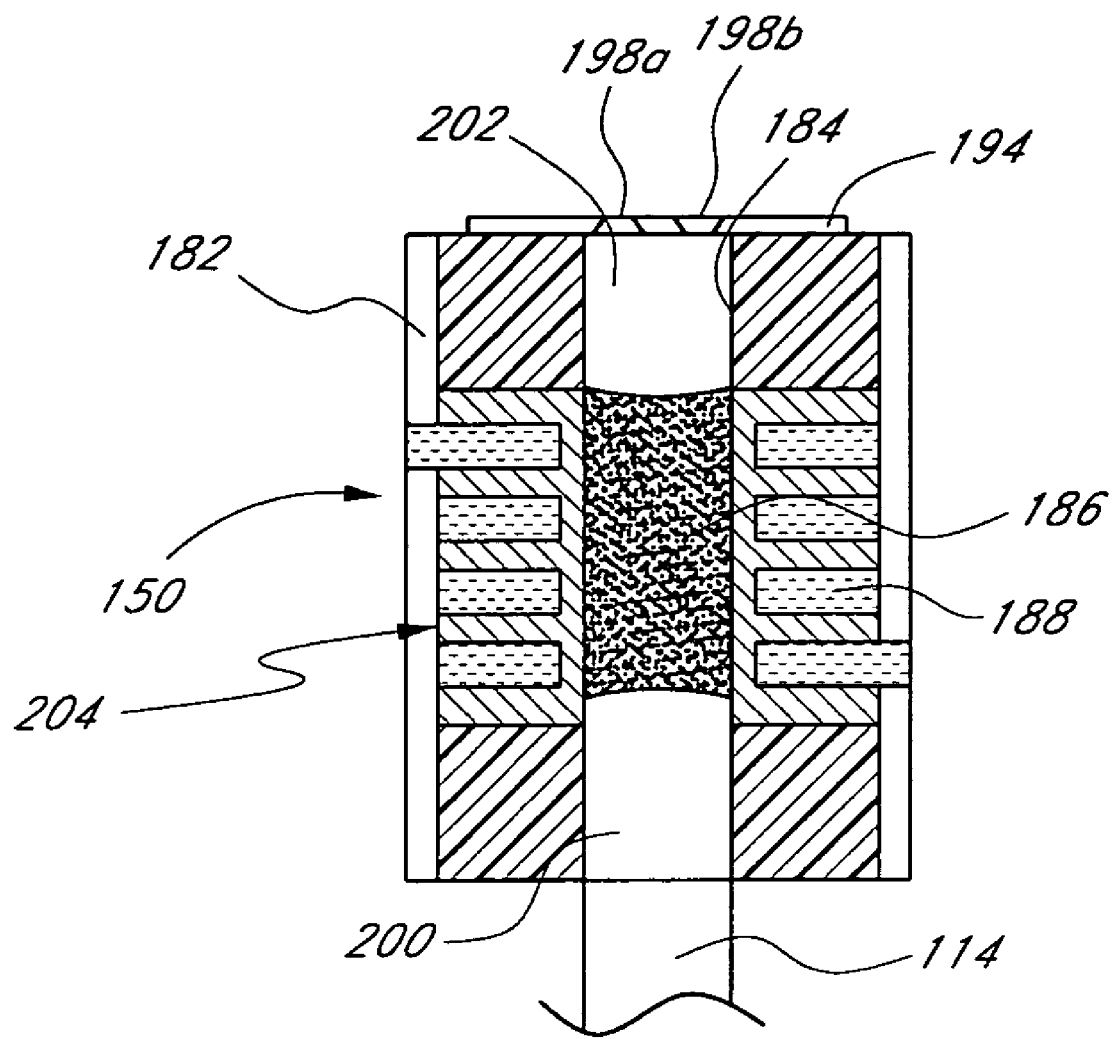
FIG. 8 is a schematic illustration of the engine that is used with the compressor in the refrigeration system and that is constructed in accordance with a preferred embodiment of the present invention.

As best seen in FIG. 8, which illustrates the engine in isolation, the resulting affinity of the liquid piston 186 to central part 188 of the cylinder creates spaces 200, 202 on the proximal and distal sides of the liquid piston 186, respectively. One or more gases occupy the proximal space. The gas can be substantially pure vapor of the fluid used for the piston or can be a different fluid. By selecting the type of gas present in the proximal space, the gas spring can have a linear (or close thereto) spring constant or a non-linear spring constant. In the illustrated embodiment, such gas or gases preferably include air and/or a vapor form of the liquid that forms the liquid piston. The laser light passes from the fiber optic 114 through gas and into the liquid rather than directly from the fiber optic 114 into the liquid. Consequently, it is preferable that the gas or vapor be substantially transparent to the laser radiation.

The volume of the proximal space 200 is on the same order of magnitude as the volume of the liquid piston 186. In the illustrated embodiment, the proximal space 200 has a diameter of about 1 mm and a length of about 1 mm.

In the illustrated embodiment, the distal space 202 functions as a variable-volume compression chamber that increases and decreases in volume as the piston 186 reciprocates within the chamber 184. The valve mechanism 196 regulates refrigerant flow into and out of the distal space 202.

The gas-filled proximal space 200 functions as a gas spring. A gas spring is also formed by the combination of the distal space 202 and the condenser 154 and the evaporator 156 that communicate with the distal space 202. The inertia of the liquid piston 186 and the compression of the gas springs 200, 202 constitute the typical components of an oscillator: the system 150 posses a well-defined natural frequency and is therefore capable of operating at resonance if excited at the right frequency. Consequently, in the present application, the liquid piston can be conceptually modeled as a mass disposed between a pair of springs. This system thus will have a natural frequency ($f_n$), which can be approximated by equation 1:

$$f_n = \frac{1}{2\pi}\sqrt{\left(\frac{P_o}{L_{liq}\rho}\right)\left(\frac{L_{gas}}{L_{gas1}L_{gas2}}\right)} \quad [1]$$

where:
$P_o$ is the system average pressure;
$L_{liq}$ is the length of the liquid piston 186;
$\rho$ is the density of the liquid of the liquid piston 186;
$L_{gas}$ is the combined length of the two gas springs 200, 202;
$L_{gas1}$ is the length of proximal gas spring 200; and
$L_{gas2}$ is the length of the distal gas spring 202.

While in the illustrated embodiment, the distal gas spring 202 is disposed on the distal side of the piston 186, other types of spring mechanism can also be used. For example, as illustrated, an elastic diaphragm (see FIGS. 10A and 10B and associated description provided below) can replace the distal gas spring of the present embodiment.

As seen in FIG. 8, the housing 182 also includes a cooling jacket 204 to cool at least the central part 188 of the housing 182. In the illustrated embodiment, the cooling jacket 204 includes a one or more microchannels cut into the central part 188, preferably using an etching technique. The cooling jacket 204 receives coolant (e.g., saline) either from the catheter coolant delivery lumen 138 or from the condenser 154 and returns it to the coolant return lumen 140. To further facilitate removal of heat from the engine 150, the central part 188 of the housing 182 preferably is formed of a material having a relatively high heat transfer coefficient.

Laser light energy pulses are delivered via the optical fiber 114 to the free surface at the proximal end of the liquid piston 186. For this purpose, the waveguide can either include: (1) a focusing lens that focuses the light beam to a diameter substantially matching the diameter of the chamber 184 at a location near (but distal of) the proximal end of the chamber 184; or (2) a collimating lens that aligns the beam emitted from the distal end of the optical fiber 114, which has a core diameter substantially equal to the diameter of the chamber 184. In this manner, the laser energy is directed to heat generally the entire area of the free surface that faces the optical fiber 114.

The liquid absorbs sufficient laser energy to superheat (instantly vaporize) the liquid to a depth of at least 0.1 of the wavelength of the laser light. The absorption characteristics of the liquid material and the high energy density of the laser are such that the absorption results in rapid formation of a superheated layer which converts liquid into gas. As the liquid is vaporized, the liquid beneath is exposed to the laser light and the superheated layer effectively migrated further into the liquid piston 186 (like the sparks of a burning fuse migrating along the length of the fuse). The migration of the superheated layer is extremely fast such that the vaporized portion of the piston 186 rapidly increases the pressure within the proximal space in a manner akin to an explosion. While vaporization is rapid, the duration of vaporization is limited by the duration of the laser pulse. Accordingly, only a small fraction of the liquid piston 186 is vaporized by any given laser pulse. The vaporized portion preferably represents between about 0.05% and 5% of the liquid piston 186 by volume, and more preferably between about 0.1% and 1% by volume. The remaining portion of the piston 186 (still in liquid phase) is sufficiently long to serve as a piston and to perform mechanical work (e.g., compress the fluid in the distal space). Typically, the length of the vaporized portion of the liquid piston 186 may be greater than 50 μm, more preferably between 0.5 and 5 mm, and most preferably about 1 mm.

Similarly, the liquid piston 186 should have a diameter sufficient to perform its function. In general, the greater the diameter of the liquid piston 186, the more power can be produced by the engine. At some point, however, increasing the diameter of the liquid piston 186 will lead to loss of capillary action, depending upon the surface tension of the liquid and the affinity of the central part 188 therefor, leading to loss of the liquid piston's integrity during operation. The liquid piston 186 preferably behaves generally as a "plug flow" with a defined boundary layer around its periphery. The thickness of the boundary layer will depend upon the liquid's density and viscosity and upon the system's frequency, as understood from the following equation:

$$\lambda = \sqrt{\frac{2\mu}{\omega\rho}} \quad [2]$$

where:
$\lambda$=thickness of boundary layer
$\mu$=viscosity of the liquid
$\omega=2\pi$ times the system's frequency (e.g., the natural frequency (see Equation [1]))
$\rho$=density of the liquid The boundary layer in the illustrated embodiment has a thickness $\lambda$ on the order of fractions of microns. Consequently, the piston 186 oscillates generally as a mass plug.

In the illustrated embodiment, where the distal space directly communicates with the heat exchangers of the refrigeration system 112, the liquid of the liquid piston 186 preferably is the same refrigerant used in the refrigeration system. In one preferred mode, the refrigerant liquid comprises R-134a, having the chemical formula $C_2H_2F_2$, a critical temperature of 101.2° C. and an estimated practicable superheat limit of about 64° C. (based upon 90% of the critical temperature in Kelvin), as compared to its normal boiling point of −26.5° C. under standard conditions. In another preferred mode, the refrigerant liquid comprises R-12, having the chemical formula $CCl_2F_2$, a critical temperature of 112° C. and an estimated practicable superheat limit of about 74° C. (based upon 90% of the critical temperature in Kelvin), as compared to its normal boiling point of −30° C. under standard conditions. Additionally, the refrigerant can comprise a mixture of fluids such as R-134a, R-23, R1-4, and cryogenic fluids such as helium, hydrogen, neon, nitrogen, and argon. The refrigerant mixture allow the refrigerator to reach temperature as low as 70° K as taught in U.S. Pat. No. 5,579,654, entitled CRYOSTAT REFRIGERATION SYSTEM USING MIXED REFRIGERANTS IN A CLOSED VAPOR COMPRESSOR CYCLE HAVING A FIXED FLOW RESTRICTION, which disclosure is hereby incorporated by reference.

A dye preferably is added to the liquid to increase absorption of the input optical energy. To facilitate high absorption at 1.064 µm for use with a Nd:YAG laser, one of the following near infrared (NIR) dyes can be added to the liquid: SDA8080 and DSB6592, both available commercially from H.W. Sands Corp., of Jupiter, Fla. The concentration of the dye in the refrigerant can be tailored to match the required optical density (e.g., 50 µm optical density).

The laser 102, which supplies the energy to drive the compressor engine 150, produces short pulses having a duration of less than 100 nanoseconds, and preferably about 50 nanoseconds to ensure rapid formation of the superheated layer and resulting gas bubble. The frequency of the laser pulses substantially matches the natural frequency of the liquid piston 186, which is, in turn, a product of the speed of explosive vaporization and the size and mass of the liquid piston and gas springs, as described above. Heat introduced into the oscillating system by the laser is removed by the cooling jacket described above.

In the illustrated embodiment, the laser 102 is a Q-switched solid state Nd:YAG laser that outputs 35 Watts of optical power at a wavelength of 1.064 µm. Although the preferred embodiment utilizes a solid-state Nd:YAG laser, other types of lasers can be used, including laser diodes and gas lasers. The Nd:YAG laser provides pulses at a repetition rate of about 20 kHz to oscillate the liquid piston 186 at its natural frequency. The energy provided per pulse preferably is about 1.75 millijoules. The energy density preferably is sufficient to vaporize during a single pulse substantially the entire area of proximal liquid surface (approximately 0.8 mm$^2$) to a depth 50 µm, starting from a liquid temperature around ambient (e.g., body temperature: 37° C.). When using a Nd:YAG laser, the vaporized layer is preferably between 10 nm and 100 µm, and more preferably between 1 µm and 50 µm.

The explosion pushes the liquid piston 186 distally. The liquid piston 186 rebounds, moves proximally, rebounds again, and then is driven distally again by re-firing the laser 102. With correct dimensional design and operational conditions (laser pulses synchronized with piston oscillation), undesired losses due to vapor-liquid heat and mass transfer through the liquid-vapor surfaces can be minimized and engine efficiency maximize.

If the laser pulses are all at the same energy, the oscillations amplitude will start small and within few oscillations (about 5 to 10) will reach steady state level. The exact number of oscillations to full amplitude is also influenced by heat removal characteristics and other thermophysical characteristics of the system. In the preferred embodiment, the first pulse has higher (from 2 to 5 times greater) energy then the following pulses, which helps the system reach full scale oscillations quicker.

The operation cycle of the engine running at steady state can be further understood by examining four sequential snapshots during the operation cycle. With reference to FIG. 9A, the liquid piston 186 is disposed at a generally central location within the chamber 184 and is moving proximally at this point in the cycle for reasons that will be soon apparent. The suction valve 198a in the distal plate 194 opens as the piston 186 moves proximally. This movement of the piston 186 also draws refrigerant vapor into the distal space 202 from the evaporator 156.

As seen in FIG. 9B, the laser 102 is fired when the liquid piston 186 reaches it maximal displacement in the proximal direction. The laser light, which is delivered by the optical fiber 114, passes through the proximal vapor space 200 and is absorbed in the proximal free surface of the liquid piston 186, which heats the liquid non-uniformly (i.e., the electromagnetic radiation superheats a layer of the liquid without significantly heating the adjacent portion of the liquid mass). The heating of the liquid is too fast to allow normal boiling and about 50 µm on the surface is vaporized by heating to the liquid superheat limit. In the illustrated embodiment, the vaporized layer preferably represents about 1% the liquid piston volume. Within one microsecond the superheated layer causes vaporization to create a large pressure rise in the proximal space. The explosive bubble following superheating thus provides a propulsive force to move the unvaporized remainder of the liquid piston 186.

Under the action of the high pressure in the proximal space 200, the liquid piston 186 starts moving distally, as seen in FIG. 9C. During the piston's distal travel (as well as during its proximal travel), the liquid mass exhibits a plug flow profile with a defined boundary layer around the perimeter, as noted above. Cohesive forces (e.g., viscosity), as well as its cooled temperature, tend to keep the liquid piston 186 as one continuous unit that generally moves as a monolith, thereby acting similar to a solid piston.

Distal movement of the piston 186 compresses the refrigerant vapor in the distal space 202 adiabatically (similar to a conventional positive displacement vapor compressor). The increased pressure in the distal chamber 202 closes the suction valve 198a and opens the discharge valve 198b. At least part of the kinetic energy of the moving piston 186 is returned to the piston 186 by elastic expansion of the distal gas spring 202, causing the liquid piston to move in the proximal direction. The resultant restoring force helps to push the liquid piston 186 toward its original position.

Additionally, once the piston 186 has reached the point of its maximum displacement distally, as shown in FIG. 9D, the piston 186 moves proximally. The work of expansion of the proximal chamber 200 and the condensation of refrigerant vapor on the wall of the cooled central part 188 of the housing 182 causes a pressure decrease which also has the consequence of imparting velocity to (i.e., draws) the liquid piston 186 in the proximal direction. Due to the inertia of the liquid piston 186, however, the original position of the piston is overshot and the piston 186 moves toward its maximum displacement in the proximal direction. The laser 102 once again is fired and the cycle repeats.

In the preferred embodiment, heat is actively removed from the engine 150 to maintain the body of the liquid piston 186 below its boiling point and to allow the explosively vaporized portion of the fluid to return to the liquid state, serving as a reusable fuel for continued operation. As noted above, the central part 188 of the housing 182 is preferably formed from a material that is a good conductor of heat, so as to provide a heat sink. The heat sink is constructed to have a large surface area and is preferably further cooled by a coolant (e.g., saline) that flows in or about the central part 188. The coolant readily removes heat from the heat sink by forced convection. With water microchannels, forced convection can remove heat at 800 W/cm$^2$, permitting continual operation at high power. The cooling system removes both the heat generated by the laser beam and the heat carried by the refrigerant pumped through the refrigeration system. According to The Second Law of Thermodynamics, the refrigerator rejected heat is at least its refrigeration power multiplied by the Carnot ratio of its operating temperatures. Stable pressure oscillations are achieved when the total heat from the laser beam and from the refrigerator (heat pump) section is balanced by the heat drawn out of the engine by the coolant flow. The coolant flow of the illustrated embodiment is capable of removing over 100 Watts of heat. The heat transfer element 144 at the catheter distal end 110 can consequently reach −100° C. and can produce cardiac tissue necrosis to a depth of greater than 10 mm.

The combined duration of the laser pulse and the explosive boiling is less than 2% of each cycle, and more preferably between 0.01% and 1% of each cycle. With the solid-state Nd:YAG laser in the illustrated embodiment, the period of the cycle is on the order of 50 microseconds, while the combined duration of the laser pulse and the explosive boiling (which occurs during the laser pulse) is in the order of 200 nanoseconds. The relatively long time period of the cycle, in comparison to the pulse duration, permits the system to react and recover before the next laser pulse is delivered.

Accordingly, in the present engine, non-uniform heating is by radiation onto a free surface of the liquid. Vapor spaces on each side of the liquid mass function as gas springs to provide a restoring force, which enables the liquid mass to enter a regime of steady state oscillations. The engine can power a compressor enormously faster and much smaller (e.g., 2-3 orders of magnitude faster and smaller) than a conventional compressor and has significantly more (e.g., ten times more) refrigeration power of a comparable Joule-Thomson expander that is commonly used in cryocatheter today. The compressor engine thus gives the present cryocatheter a greater cryoablation capacity (killing depth) than that of conventional cardiac ablation catheters.

While the illustrated embodiment is a cryocatheter, it is understood that the present refrigeration system (or engine thereof) can be incorporated into other types of medical apparatus as well. For example, the present cryocooler (i.e., refrigeration system) can be incorporated into a handheld surgical ablation probe that is substantially rigid and can be used to directly ablate cardiac tissue during trans-thoracic or minimally invasive surgery. The probe can include a deflectable tip for enhanced maneuverability and precise placement of the heat transfer element. The engine can also be used as a miniature ultrasound source for medical imaging and treatment. The laser bubble technology enables an ultrasound actuator that is significantly smaller than conventional piezoelectric ultrasound transducers. As a result, imaging catheters with the present engine can be used to provide deeper views of tissue through blood vessels.

In the refrigeration cycle, the piston requires significant displacement in order to actuate the valves and to move refrigerant through the system. The piston can have a significantly smaller displacement when the engine is used as an ultrasound transducer and can be oscillated at a frequency within the ultrasound range (for example, at 10 MHz to 40 MHz). Importantly, the amplitude of oscillation of the piston roughly matches the size of the cylinder, and accordingly, the engine can be made much smaller than a conventional piezoelectric transducer where the amplitude of oscillation represents only a 0.2% volume change of the total transducer volume. For example, the engine may be 100 times smaller than the piezoelectric transducer used for similar imaging purposes.

Another embodiment of the engine compressor is illustrated in FIGS. 10A and 10B. Where appropriate, like reference numbers with a suffix "a" have been used to indicate like parts of the two embodiments for ease of understanding. The foregoing description thus should be understood to apply equally to like parts of the present embodiment.

A diaphragm 300 distal of the liquid piston 186a separates the liquid piston 186a from the refrigerant. This diaphragm 300 can be made of a composite of silicon rubber and NiTi flexure. A similar microdiaphragm is FDA approved and is currently used in other implantable devices.

Movement of the piston 186a causes the diaphragm 300 to flex proximally and distally to increase and decrease, respectively, the volume in a compressor chamber 302 that is located on the distal side of the diaphragm 300. Distal movement of the diaphragm 300 adiabatically compresses the refrigerant within the compressor chamber 302, which is discharged from the compressor chamber 300 through the discharge valve 304. Proximal movement of the diaphragm 300 draws refrigerant vapor into the pump chamber 302 through the suction valve 306.

Water-based liquids can absorb and remove about five times more heat than a comparable amount of refrigerant, such as R-134a. Therefore, a variation of the embodiment illustrated in FIG. 10A can utilize dyed saline as the liquid piston of the engine.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present engine has been described in the context of particularly preferred embodiments, the skilled artisan will appreciate, in view of the present disclosure, that certain advantages, features and aspects of the engine may be realized in a variety of other applications, many of which have been noted above. For example, while particularly useful for small-scale applications (e.g., chamber volumes of less than 2 cm$^3$), such as the illustrated medical application, the skilled artisan can readily adopt the principles and advantages described herein to a variety of other applications, including larger scale devices. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. An engine comprising:
   a housing having one or more chamber walls that define a chamber within the housing;
   a liquid piston disposed within the chamber, the liquid piston having at least one free surface not in contact with the chamber wall;
   a laser energy source positioned to directly heat the free surface of the liquid piston;
   a gas spring positioned within the chamber adjacent the free surface of the liquid piston and within the propagation path of the laser energy; and
   a spring mechanism positioned within the housing to exert pressure on another surface of the liquid piston, the spring mechanism comprising a flexible diaphragm disposed adjacent said another surface of the liquid piston.

2. An engine comprising:
   a housing having one or more chamber walls that define a chamber within the housing;
   a liquid piston disposed within the chamber, the liquid piston having at least one free surface not in contact with the chamber wall;
   a laser energy source positioned to directly heat the free surface of the liquid piston;
   a gas spring positioned within the chamber adjacent the free surface of the liquid piston and within the propagation path of the laser energy; and
   a spring mechanism positioned within the housing to exert pressure on another surface of the liquid piston, the spring mechanism comprising a second gas spring.

3. The engine as in claim 2, wherein the first and second gas springs are symmetrically disposed relative to the liquid piston.

* * * * *

UNITED STATES PATENT AND TRADEMARK OFFICE
CERTIFICATE OF CORRECTION

PATENT NO.       : 7,615,048 B2                                       Page 1 of 1
APPLICATION NO.  : 11/210215
DATED            : November 10, 2009
INVENTOR(S)      : Ran Yaron It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1024 days.

Signed and Sealed this

Nineteenth Day of October, 2010

David J. Kappos
*Director of the United States Patent and Trademark Office*